(12) United States Patent
Fudim (10) Patent No.: US 8,602,783 B2
(45) Date of Patent: Dec. 10, 2013

(54) IMPRESSION GINGIVAL CUFF FOR DENTAL IMPLANTS

(76) Inventor: Zvi Fudim, Dollard-des-Ormeaux (CA)

( * ) Notice: Subject to any disclaimer, the term of this patent is extended or adjusted under 35 U.S.C. 154(b) by 0 days.

(21) Appl. No.: 13/278,804

(22) Filed: Oct. 21, 2011

(65) Prior Publication Data

US 2013/0101964 A1    Apr. 25, 2013

(51) Int. Cl.
*A61C 9/00* (2006.01)
(52) U.S. Cl.
USPC .......................................... 433/214; 433/173
(58) Field of Classification Search
USPC ............... 433/71, 213–214, 34–41, 172–174, 433/201.1
See application file for complete search history.

(56) References Cited

U.S. PATENT DOCUMENTS

| | | | | |
|---|---|---|---|---|
| 2,092,549 | A * | 9/1937 | Craigo | 433/136 |
| 3,238,620 | A * | 3/1966 | Robertson | 433/40 |
| 3,304,608 | A * | 2/1967 | Frohnecke | 433/40 |
| 3,390,458 | A * | 7/1968 | Lytton | 433/40 |
| 3,471,058 | A * | 10/1969 | Latham et al. | 222/92 |
| 3,530,585 | A * | 9/1970 | Goldstine | 433/40 |
| 3,541,689 | A * | 11/1970 | Snead | 433/40 |
| 3,548,500 | A * | 12/1970 | Cohen | 433/218 |
| 3,686,754 | A * | 8/1972 | Kondoloff | 433/223 |
| 4,253,829 | A * | 3/1981 | Adelberger | 433/40 |
| 4,373,915 | A * | 2/1983 | Comstock | 433/136 |
| 4,424,034 | A * | 1/1984 | Korwin et al. | 433/40 |
| 4,465,462 | A * | 8/1984 | Ticknor | 433/136 |
| 4,531,914 | A * | 7/1985 | Spinello | 433/136 |
| 5,338,198 | A | 8/1994 | Wu et al. | |
| 5,360,341 | A * | 11/1994 | Abramowitz | 433/215 |
| 5,499,918 | A * | 3/1996 | Morgan et al. | 433/173 |
| 5,676,543 | A * | 10/1997 | Dragan | 433/136 |
| 5,749,731 | A * | 5/1998 | Morgan et al. | 433/173 |
| 6,155,828 | A * | 12/2000 | Lazzara et al. | 433/173 |
| 6,558,162 | B1 | 5/2003 | Porter et al. | |
| 6,769,913 | B2 * | 8/2004 | Hurson | 433/173 |

(Continued)

FOREIGN PATENT DOCUMENTS

FR    2860421    4/2005
WO    0217814    3/2002

OTHER PUBLICATIONS

The International Journal of Oral & Maxillofacial Implants, vol. 23, Nov. 2008.
JADA 2008, vol. 139, Oct. 2008, 1354-1363.

*Primary Examiner* — Cris L Rodriguez
*Assistant Examiner* — Matthew Saunders
(74) *Attorney, Agent, or Firm* — Goudreau Gage Dubuc; Gonzalo Lavin (57) ABSTRACT

An impression gingival cuff for taking an impression during a restoration procedure of a dental implant osteointegrated in a jaw bone. The dental implant is engageably connectable with an abutment having a prominent countour. The impression gingival cuff has a tubular-conical shape, a circumferential thin wall, two open ends including an apical end oriented towards a tooth root and a proximal end oriented towards an occlusal direction, an inner surface oriented towards the abutment and an outer surface oriented towards surrounding gingival tissue. During installation of the cuff between the dental implant and the abutment, the apical end retains the prominent contour of the abutment so that the outer surface of the cuff pushes the surrounding gingival tissue away from the abutment. This allows taking an accurate impression of both the dental implant and abutment in order to fabricate a high precision restoration.

5 Claims, 7 Drawing Sheets

(56) References Cited

U.S. PATENT DOCUMENTS

| | | |
|---|---|---|
| 6,790,040 B2 | 9/2004 | Amber et al. |
| 2002/0106610 A1* | 8/2002 | Hurson .......................... 433/173 |
| 2003/0190584 A1* | 10/2003 | Heasley ........................ 433/136 |
| 2004/0265777 A1* | 12/2004 | Heasley ........................ 433/136 |
| 2005/0175962 A1* | 8/2005 | Haje ............................. 433/136 |
| 2007/0196785 A1* | 8/2007 | Matheson ..................... 433/136 |
| 2009/0075240 A1* | 3/2009 | Discko et al. ................. 433/215 |

* cited by examiner

IMPRESSION GINGIVAL CUFF FOR DENTAL IMPLANTS

CROSS-REFERENCE TO RELATED APPLICATIONS

This application claims benefit of provisional application No. 61/406,159 filed on Oct. 24, 2010.

BACKGROUND OF THE INVENTION

1. Field of the Invention

The present invention relates generally to dental implants and, more particularly, methods and devices for impression to restore dental implants. It comes to solve: mould inaccuracies, cost, labour time and infection control problems.

2. Description of Prior Art

"Several impression techniques are used in implant dentistry while some require gingival displacement while making impressions. Others, such as the pickup impression technique, do not require any gingival retraction. However, this pickup impression technique requires use of additional parts such as: implant analog, impression copings, and impression transfers which have an impact on accuracy and cost of the restoration.

For all screw retained implant restorations, most systems use mechanical components (impression copings and transfers) that can be adapted accurately and directly to the proximal end of the implant or indirectly to the abutment fixture.

With cement-retained prostheses that use customized abutments, the pickup impression technique cannot be used owing to the unique contour of the abutments.

Another important aspect of different impression techniques is the inaccuracy that they all present. Perfect passive fit in the interface between an abutment and an implant is difficult to obtain due to the different factors that affect the process of prostheses fabrication, such as different system tolerance, type of abutment, properties of metallic alloy, impression materials, investing, and casting problems. Moreover, abutment position distortion has often accompanied transfer impression techniques. (The International Journal of Oral & Maxillofacial Implants, volume 23, November 2008).

The ability of the clinician to perform impression related procedures is fundamental for the quality of the prosthesis. Therefore, clinicians must use another technique such as the conventional crown and bridge impression or optical impression.

To ensure accuracy with polyvinylsiloxane impression materials, clinicians must maintain a minimum bulk of 0.2-millimeter thickness in the sulcus area, which they can achieve by retracting the gingiva for at least four minutes before making the impression. Rapid closure of the sulcus requires that clinicians make the impression immediately after removing the retraction material.

Larger sulcus spaces than necessary for conventional crown and bridge impression techniques are needed when making digital computer aided design/computer-aided manufacturing (CAD/CAM) impressions (U.S. Pat. No. 5,338,198, patented Aug. 16, 1994 by DACAM Laboratory Inc.) to ensure accurate recording of finishing lines.

Direct optical impressions are limited to line of sight, which is facilitated by performing gingival retraction to expose finish lines.

Artifacts caused by retraction cord fibres that remain in the sulcus may affect the accuracy of optical impressions.

15% aluminum chloride in an injectable kaolin matrix leaves a clean sulcus, reducing the influence of artefact generated errors.

However, the powders used when making optical impressions to reduce reflectivity and make tooth surfaces measurable can influence impression accuracy by increasing tooth surface thickness.

Clinicians regard the indirect capture of digitized information as being potentially more accurate; however, the way in which clinicians can acquire data is influenced by the thickness of the impression material in the sulcus area. Significant errors can result from thin impression margins with a radius less than the contacting probe tip.

Indirect scanable body impressions (U.S. Pat. No. 6,558,162 patented May 6, 2003 and U.S. Pat. No. 6,790,040, patented Sep. 14, 2004 by Implant Innovations Inc) have so far very good clinical results. However, that particular method does not require gingival displacement. Unlike direct impression techniques, the indirect scanable body does not retrieve any information about the abutment what may be in some cases indispensable mostly for the aesthetics.

Gingival Retraction Technique

When making impressions for fixed prostheses, clinicians need to expose access and isolate the abutment margins. Clinicians can record good impressions only if they meet these requirements. The precise reproduction of the abutment provides clinicians with crucial clinical information that allows them to fabricate exact-fitting, biointegrated restorations. The aim of gingival retraction is to atraumatically allow access for the impression material beyond the abutment margins and to create space so that the impression material is sufficiently thick so as to be tear-resistant. In peridental tissue, the fibre-rich, highly organized periodontal complex surrounding natural teeth provides support for gingival tissues when they are retracted, mitigating the collapse of the tissues when the retraction agents are removed before making the impression. The implant surrounding fibre structure, however, does not provide the same level of support and is not able to prevent the collapse of retracted tissues to the same extent, which complicates attempts to successfully make impressions. This is particularly true in situations in which the depth of sulcus is greater than average, such as when an implant has been placed deeply.

Clinicians prefer that patients have a greater degree of soft-tissue support than that found around natural teeth when they retract soft tissues surrounding implants. Yet at the same time, clinicians need to ensure that the retraction forces are gentle since patients' perimplant junctional epithelium is more fragile.

Deformation of gingival tissues during retraction and impression procedures involves four forces: retraction, relapse, displacement and collapse.

Retraction is the downward and outward movement of the free gingival margin that is caused by the retraction material and the technique used.

Relapse is the tendency of the gum to go back to its original position. It is influenced by the elasticity or memory of the tissue and by the rebound forces of adjacent attached gingiva that was compressed during retraction. A 0.2-mm sulcular width is necessary for there to be sufficient thickness of material at the margins of impressions so they can withstand tearing or distortion on removal of the impression.

Displacement is a downward movement of the gum that is caused by heavy-consistency impression material bearing down on unsupported retracted gingival tissues.

Collapse is the tendency of the gum to flatten under forces associated with the use of closely adapted customized impression trays.

Depending on the amount and duration of these forces, the gingival tissue may or may not rebound to its original position. The gingival tissue responds viscoelastically, and recovery time is much longer than the duration of the deforming force application. If too much trauma occurs and if the gingival tissue is too thin, irreversible alteration will take place.

Clinicians have adopted techniques that originally were designed for natural teeth for use in implant restoration situations despite significant differences between the tooth gum and the implant surrounding tissue. Techniques that clinicians have refined to work well for teeth may not address the challenges faced by clinicians in implant dentistry. The following sections review the available retraction techniques for natural teeth and their potential application for implant restorations:

1. Mechanical Retraction

Cord: Clinicians place retraction cords by using cord-packing instruments; however, many commonly used hand instruments (such as the Hollenbach carver tip) were not designed for this application. The forces generated by pointed or wedge-shaped instrument tips may be traumatic to the relatively fragile junctional epithelium around implants, whereas tooth's gingival tissues may be more forgiving of this type of force. Some manufacturers make purpose-designed packing devices that have smooth, non serrated circular heads that can be used to place and compress twisted cord with a sliding motion. Other manufacturers make devices with serrated circular heads for use with braided cords. The thin edges of these serrated circular heads sink into the braided cord, and the fine serrations keep it from slipping off and cutting the gingival attachment. There is no literature describing the use of cord-packing instruments, and the forces involved with cord placement remain undetermined.

Single-Cord Versus Dual-Cord Technique:

Retraction cords were developed for use with natural teeth. They provide more effective control of gingival hemorrhage and exudates when used in conjunction with drugs than when used with no drugs. The use of a single retraction cord often provides inadequate gingival retraction. The dual-cord technique in which the first cord remains in the sulcus reduces the tendency for the gum to recoil and partially displace the setting impression material. Results from one survey showed that 98 percent of prosthodontists use cords, with 48 percent using a dual-cord technique and 44 percent using a single-cord technique.

Placement of retraction cords can cause injury to the sulcular epithelium and underlying connective tissues, as shown by the results of experiments involving dogs' teeth. The filaments or fibres of conventional cords also may cause residual contamination of sulcular wounds, creating foreign body reactions and exacerbating inflammation. Healing of the sulcus can take seven to 10 days. Use of minimal force is necessary when packing cords to protect Sharpey fibres, and application of excessive force is inappropriate because it may cause bleeding, gingival inflammation and shrinkage of marginal tissues.

Clinicians should question the use of cords around implants since the junctional epithelium is not attached to the implant, is more permeable and has a lower regenerative capacity than the junctional epithelium around teeth.

2. Chemical-Mechanical Retraction

Chemicals with cord: Epinephrine commonly is used to medicate retraction cords since it provides effective vasoconstriction and haemostasis during retraction. It is, however, associated with significant local and systemic side effects, which investigators have reported occurring during 33 percent of applications.

Clinicians should avoid applying high concentrations of epinephrine to large areas of lacerated or abraded gingival tissues. Patients who are susceptible to the effects of epinephrine may develop "epinephrine syndrome," which includes tachycardia, rapid respiration, increased blood pressure, anxiety and postoperative depression.

A number of alternatives to epinephrine are used clinically, with varying benefits and drawbacks.

Synthetic Sympatho-Mimetic agents: that mimic the actions of epinephrine are more effective and safer than epinephrine.

Aluminum Sulphate and aluminum potassium sulphate: act by precipitating tissue proteins with tissue contraction, inhibiting transcapillary movement of plasma proteins and arresting capillary bleeding. Both are haemostatic and retractile, which causes minimal postoperative inflammation at therapeutic concentrations, although concentrated aluminum potassium sulphate solutions can cause severe inflammation and tissue necrosis.

Aluminum Chloride: the action of aluminum chloride is similar to that of aluminum sulphate, which is an astringent that causes precipitation of tissue proteins but less vasoconstriction than epinephrine.

Aluminum chloride is the least irritating of the medicaments used for impregnating retraction cords, but it disturbs the setting of polyvinylsiloxane impression materials.

Aluminum potassium sulphate and aluminum chloride medicated cords are more effective in keeping the sulcus open after clinicians remove the cord than are epinephrine-medicated cords.

Ferric Sulphate: owing to its iron content, ferric sulphate stains gingival tissues a yellow-brown to black color for several days after a clinician has used it as a retraction agent. The accuracy of surface detail reproduction during impressions can be modified by ferric sulphate, as it disturbs the setting reaction of polyvinylsiloxanes. Thus, it is important for clinicians to remove all traces of medicament from the tissues carefully before recording the impressions.

The two main drawbacks of using chemicals with retraction cords are: a) the occurrence of rebound hyperaemia that often occurs after cord removal, which affects how effectively clinicians can make impressions, and b) inflammatory reactions induced by these chemicals, which can affect the sub epithelial connective tissue. When clinicians consider all of these factors, they may question whether retraction cords are appropriate for use around implants, given the vulnerability of the junctional epithelium.

Chemicals in an injectable matrix: Injecting 15 percent aluminum chloride in a kaolin matrix opens the sulcus, providing significant mechanical retraction. When compared with having a cord packed into the sulcus, an injection of 15 percent aluminum chloride in a kaolin matrix resulted in less pain for patients and was easier and quicker to administer. Furthermore, its effectiveness in reducing the flow of sulcular exudates is similar to that of epinephrine-soaked cords.

The use of 15 percent aluminum chloride in an injectable kaolin matrix is effective. It is also safe, with the results of one study showing no reports of adverse effects. Gingival recession associated with an injection of aluminum chloride into the gingival sulcus is almost undetectable. The injectable matrix is hydrophilic and can be flushed away relatively easily from the gingival crevice. As with any foreign materials introduced into the oral cavity, there remains a small risk of residues' persisting in the gingival crevice. The viscosity of the injectable matrix may not be enough to provide sufficient retraction for deeper subgingival reparations, and aluminum chloride can inhibit the set of polyether and polyvinylsiloxane materials if clinicians do not rinse it away properly before making impressions.

The delivery of chemicals via an injectable matrix shows promise for implant surrounding tissue retraction, because it preserves the gingival tissues with no risk of lacerating or inflaming the junctional epithelium. In patients who have deeply placed implants with subgingival margins, however, its value may be somewhat limited by the extent to which such matrices are able to retract effectively.

An inert matrix: a polyvinylsiloxane material for gingival retraction was introduced in 2005. It works by generating hydrogen, causing expansion of the material against the sulcus walls during setting. The manufacturer has reported advantages including gentle placement without need for local anaesthesia, visibility in the sulcus due to its bright color, ease of removal and absence of the need for haemostatic medicaments. Potential drawbacks are that it may not improve the speed or quality of retraction obtained and that it likely is less effective with subgingival margins. Clinicians place deep implants with subgingival margins relatively frequently since implant placement is dictated largely by the location of available bone.

3. Surgical Retraction

Lasers: Compared with other retraction techniques, diode lasers with a wavelength of 980 nanometers and neodymium: Yttrium-Aluminum-Garnet (Nd:YAG) lasers with a wavelength of 1,064 nm are less aggressive, cause less bleeding and result in less recession around natural teeth (2.2 percent versus 10.0 percent).

The use of Nd:YAG lasers is contraindicated near implant surfaces, because they tend to absorb energy, which causes them to heat up and transmit the heat to bone, owing to the effects of this laser's wavelength on metal. There is also a tendency for Nd:YAG lasers to damage the fragile sub junctional epithelium at the sulcus base around implants.

Erbium:Yttrium-Aluminum-Garnet (Er:YAG) lasers with a wavelength of 2,940 nm are reflected by metal implant surfaces and minimally penetrate the soft tissues, so they are relatively safe to use. The haemostasis achieved with the Er:YAG laser, however, is not as effective as that achieved with the carbon dioxide ($CO_2$) laser.

The prime chromophore of the $CO_2$ laser, which has a wavelength of 10,600 nm, is water, and it reflects off metal surfaces. When used near metal implant surfaces, $CO_2$ lasers absorb little energy, with only small temperature increases (<3° C.) and minimal collateral damage. $CO_2$ lasers do not alter the structure of the implant surface.

Surgical wounds created by lasers heal by secondary intention, and incision lines show disorganized fibroblast alignment. This reduces tissue shrinkage through scarring, which helps preserve gingival margin heights.

Although there is a hemidesmosornal attachment around implants that creates a biological seal, the attached gingiva serves as a barrier that prevents exposure of the implant body over time through recession.

There are many advantages to using $CO_2$ lasers, but their method of exposing implant margins is to create a trough by excision rather than by displacing soft tissue. Therefore, their use may not be practical around deeply placed implant fixtures where a large defect could result. In addition, in anterior applications in which aesthetics is critical, it may not be desirable to create a trough around the margins, as it may have a detrimental effect on patients' appearances.

Although $CO_2$ lasers may be significantly useful in some implant impression situations, they are invasive, thus failing to meet the ideal objective of a truly conservative technique.

Electrosurgery: Clinicians can use Electrosurgery effectively to widen the gingival sulcus around natural teeth before placing the cord and to provide haemostasis by coagulation. However, Electrosurgery is not recommended around implants because there is significant risk that the contacting electrode may arc by conducting electric current though the metal implant structure to the bone rather than via the more dispersive gingival tissue pathway. The concentrated electrical current at the tip of electrodes can generate heat, which may cause osseous or mucosal necrosis.

Rotary curettage: Rotary curettage involves the use of a high-speed turbine to excise the gingival tissue quickly and create a trough around the margins. For healthy, disease-free tissue around natural teeth, rotary curettage has little effect on gingival margin heights if adequate keratinized gingiva is present, although slight deepening of the sulcus may result. However, rotary curettage is inappropriate for use around implant restorations because of poor tactile control when cutting soft tissue, which could lead to bur contact damage to the implant surface and over instrumentation. The absence of keratinized gingiva at the base of the gingival sulcus surrounding the implant could lead to an exaggerated response to rotary curettage, including deepening of the sulcus and gross recession."

From JADA 2008, volume 139, October 2008; 1354-1363

SUMMARY OF THE INVENTION

The main purpose of the invention is to displace the soft tissue that surrounds the implant abutment allowing the impression means (conventional or digital) to have an access to the surface of the abutment needed for optimal restoration. It comes to solve: mould inaccuracies, infection control problems, and costs comprising material costs, chair time, labour time.

Another object of the present invention is to simplify the process of taking impression of an implant abutment for cement retained restoration using the same method of impression as for natural teeth.

Another object of the present invention is to implement the impression method which comprising following steps:

1. After the completion of the osteointegration, the healing abutment is removed and the right abutment is chosen.

2. The abutment is installed and the relations between the maxillaries are verified.

3. The size and the angle of the abutment are examined as well as the relation between the abutment and the surrounding soft tissue in order to obtain desirable emergence profile.

4. By necessity, the abutment is customized by trimming and grinding process.

5. Once the abutment fits well, it is removed from the implant. A sterile Impression Gingival Cuff is placed on the distal (apical) end of the implant's abutment.

6. Together with the inserted Impression Gingival Cuff, the abutment engages back to the proximal end of the implant.

7. The abutment then is fastened to the implant.

8. The low viscosity impression material is ejected in the space between and around the Impression Gingival Cuff's wall and the abutment's proximal end, following insertion of the impression tray charged with high viscosity impression material.

9. Further the complete setting of the impression material the tray removed from patient's mouth, examined and sent to the dental lab.

10. Positive stone moulds or 3D CAM models then prepared. The models are articulated and the final restoration is fabricated.

11. Once the final restoration is ready, it is sent to the dentist.

One of the advantages of the invention is that the direct impression can be taken digitally with a special digital scanner such as described in U.S. Pat. No. 5,338,198, patented Aug. 16, 1994 by DACAM Laboratory Inc.

The following embodiments present the advantages of the invention.

In accordance of one of the embodiments of the invention, the outer surface of the Impression Gingival Cuff's wall pushes the surrounding soft tissue away from the abutment due to the rigidity and form of the Impression Gingival Cuffs proximal end.

In accordance of another embodiment of the invention, the inner surface of the Impression Gingival Cuff's wall creates a room allowing an access for the impression material to enter and register the details such as: shape, size and orientation of the abutment.

In accordance of another embodiment of the invention the existence of the space between the abutment's proximal end and the wall of the Impression Gingival Cuff allows an access for the temporary acrylic material to enter the subgingival area of the abutment creating an emergence profile of the restoration.

In accordance of another embodiment of the invention, the Impression Gingival Cuff creates space between the abutment's proximal end and the wall of the Impression Gingival Cuff, building up an hydraulic pressure inside that space while the impression material in its liquid state. Due to that hydraulic pressure, there is an apical translation of the cuff allowing the impression material to advance beyond the most prominent part of the abutment.

It is another advantage of the present invention that allows restoration of abutments that comprise deep subgingival margins that usually present great difficulties for restoration in previous art methods.

It is another advantage of the present invention that does not require pain control since the placement of the Impression Gingival Cuff does not injure surrounding tissue and does not cause discomfort and pain.

It is another advantage of the present invention that does not require haemostasis since the placement of the Impression Gingival Cuff does not traumatize surrounding tissue and does not cause discomfort and pain.

It is another advantage of the present invention that does not cause discomfort to patients due to bad test unlike chemical retraction with a gingival retraction cord.

It is another advantage of the present invention that does not interfere in the process of impression material setting since it is made of inert materials.

It is another advantage of the present invention that does not affect irreversibly surrounding soft tissue morphology including shape and color unlike a retraction method with ferric sulphate.

It is an advantage of the present invention that uses direct method of impression without impression transfers, impression copings and implant analogs, which have been usually implemented in the previous art technique.

It is another advantage of the present invention that eliminates the need of a temporary abutment since the temporary restoration will be supported by the same abutment that supports the final restoration.

It is another advantage of the present invention that provides desirable conditions to create proper emergence profile bellow the soft tissue level with a temporary restoration material.

It is another advantage of the present invention that does not require any special training for dental office staff as well as for dental laboratory technicians since the impression method of the present invention does not differ from a conventional crown and bridge impression technique.

It is an advantage of the present invention that by its simplicity it is less time consuming then previous art.

It is another advantage of the present invention that does not require fabrication of custom impression trays such as "open tray".

It is another advantage of the present invention that the abutment is installed in the patient's mouth shortly after removing from a sterile package. Unlike the previous art, the abutment is not sent to the lab, and thus can be spared from contamination in the non-sterile environment.

It is another advantage of the present invention that allows instant registration of the intermaxillary relation using the permanent abutment after it has been installed and adjusted vertically.

It is another advantage of the present invention that makes possible to use "triple tray" impression technique since the customised abutment does not interfere the patient's bite.

[0053] It is another advantage of the present invention that makes possible a slow release of different drugs through the resorbable Impression Gingival Cuff by using mechanisms similar to U.S. Pat. No. 4,767,628.

It is another advantage of the present invention that allows fabrication of the analog mould of patient's mouth of one single material either dental stone or polymer. Thus, the invention eliminates problems of volume instability due to different expansion and shrinkage rates of materials used in fabrication of conventional implant mould.

BRIEF DESCRIPTION OF THE FIGURES

FIG. 3A Illustrates a section 1,1 of FIG. 3;

DETAILED DESCRIPTION OF THE ILLUSTRATED EMBODIMENTS

Figure 1:
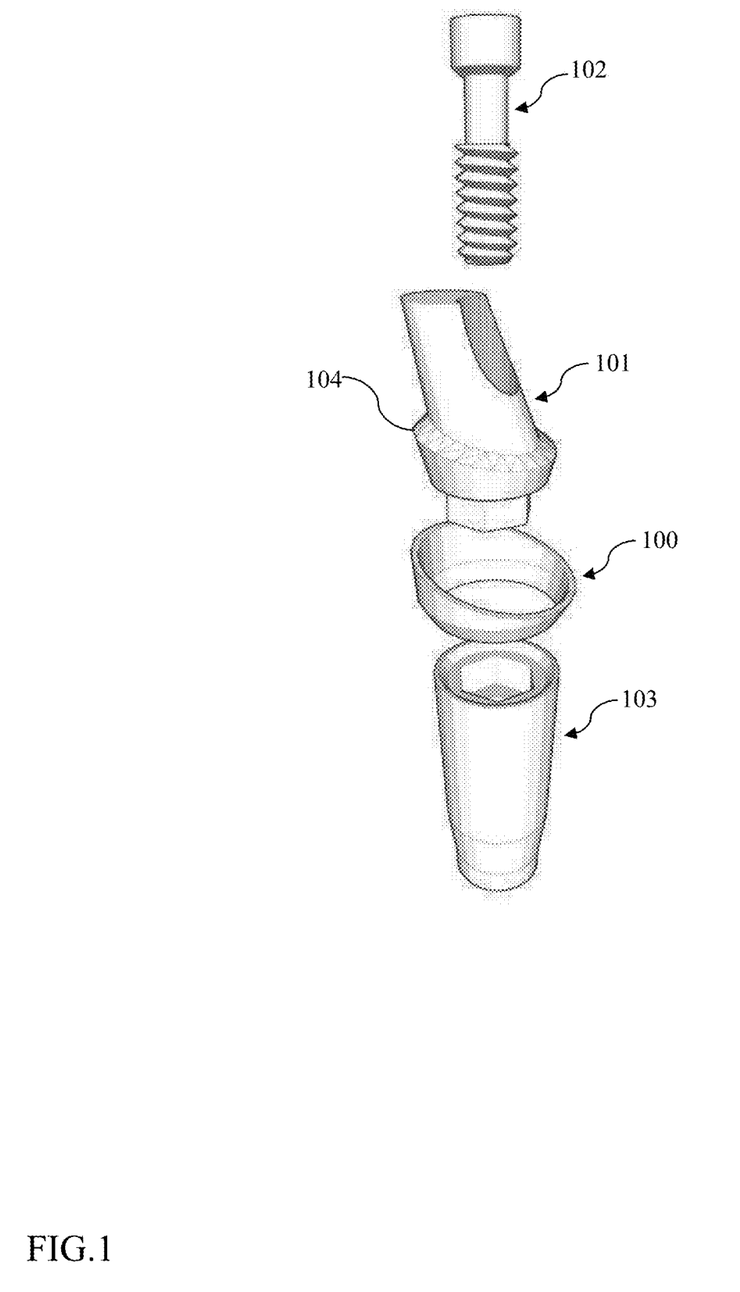
FIG. 1 Illustrates an exploded view of major components of a screw indexed dental implant.

FIG. 1 demonstrates the sequence of the assembly of a hexed-screw implant 103 and prosthetic accessories such as: an impression gingival cuff 100, an abutment 101, and a connecting screw 102.

Figure 1A:
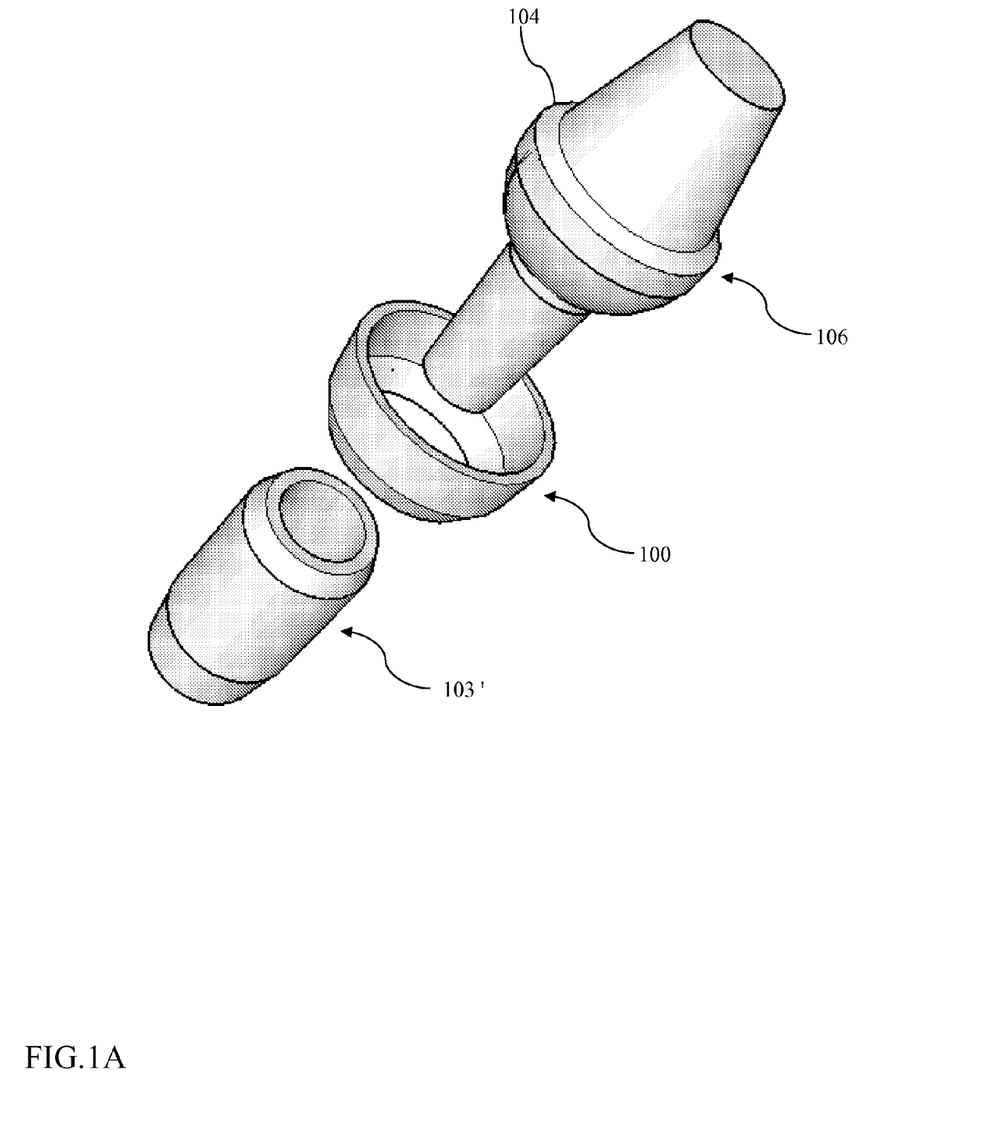
FIG. 1A Illustrates an exploded view of major components of a cone Morse non indexed dental implant.

FIG. 1A demonstrates the sequence of the assembly of cone Morse implant 103' and prosthetic accessories such as: an impression gingival cuff 100, an abutment 101.

Figure 2:
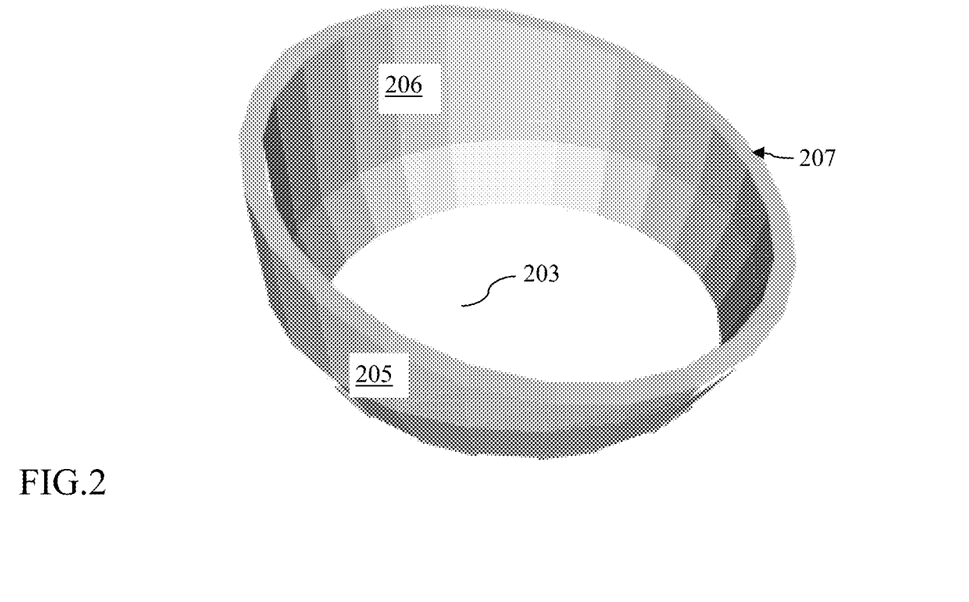
FIG. 2 Illustrates a Gingival Cuff from occlusal view.

The Impression Gingival Cuff as shown in FIG. 2 comprising an apical end 204 with apical opening 203 and an occlusal end 202 with occlusal opening 201. The main role of the apical end 204 comprises retention due to the prominent contour 104 of the abutment as it shown in FIG. 1. The outer surface 205 characterized by its convex form divergent towards occlusal. The inner surface 206 characterized by its concave form convergent towards apical.

Figure 2A:
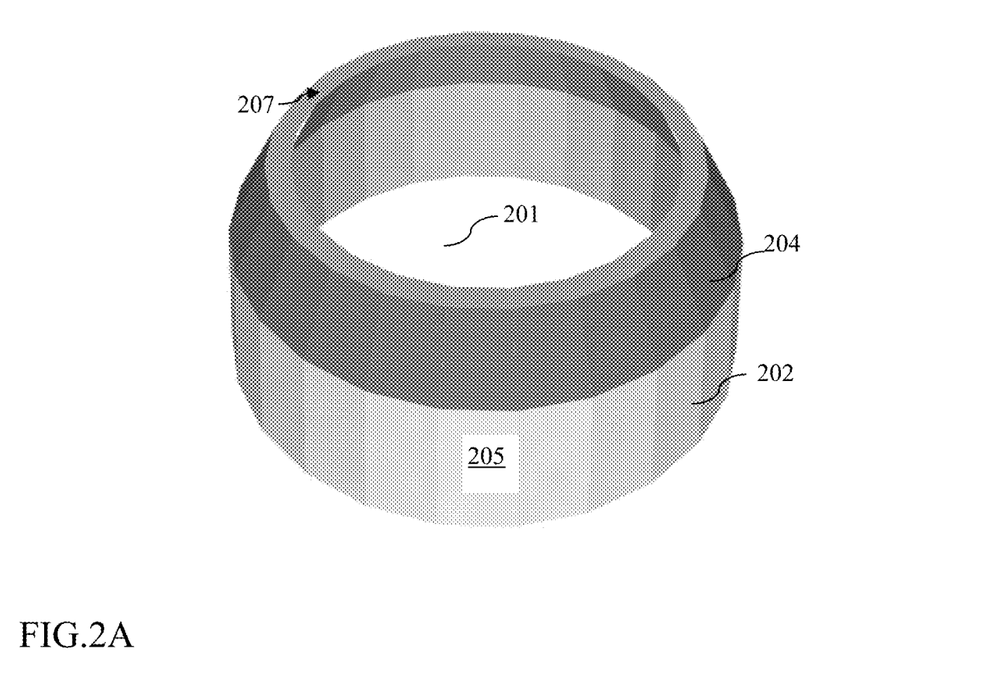
FIG. 2A Illustrates a Gingival Cuff from apical view drawing.

The Impression Gingival Cuff as shown in FIG. 2A differs from the one in FIG. 2 by the asymmetry of its wall 207. The asymmetrical wall 207 follows the thickness of the surrounding tissue, which often is not equal everywhere.

Figure 3:
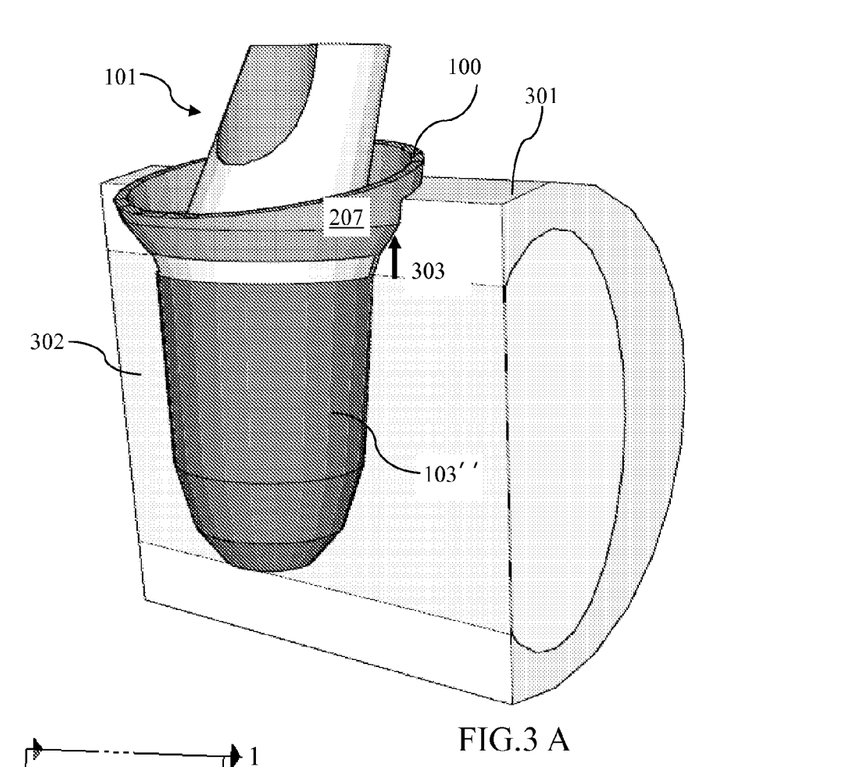
FIG. 3 Illustrates a fragment of an arc where the Gingival Cuff is mounted on the abuttment.

FIG. 3 and FIG. 3A illustrate the section 1,1 of the fragment of a patient's mouth with an osteointegrated implant 103" in a jaw bone 302 and the Impression Gingival Cuff 100 which is pushed on its wall 207 by the soft tissue 301 in occlusal direction 303 against the resistance of the abutment's most prominent contour 104 orienting the Impression Gingival Cuff vertically.

Figure 4:
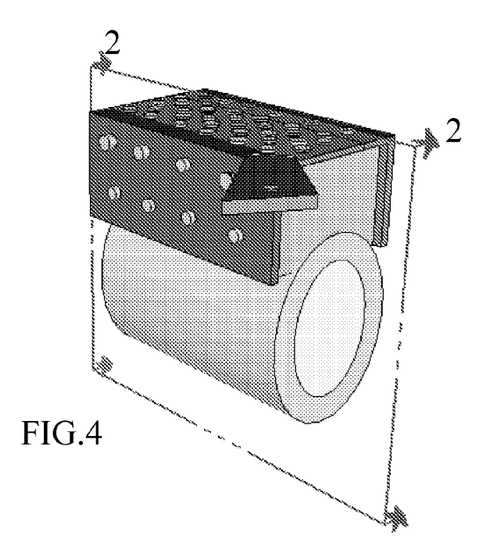
FIG. 4 Illustrates a fragment of patient's mouth during impression take.
Figure 4A:
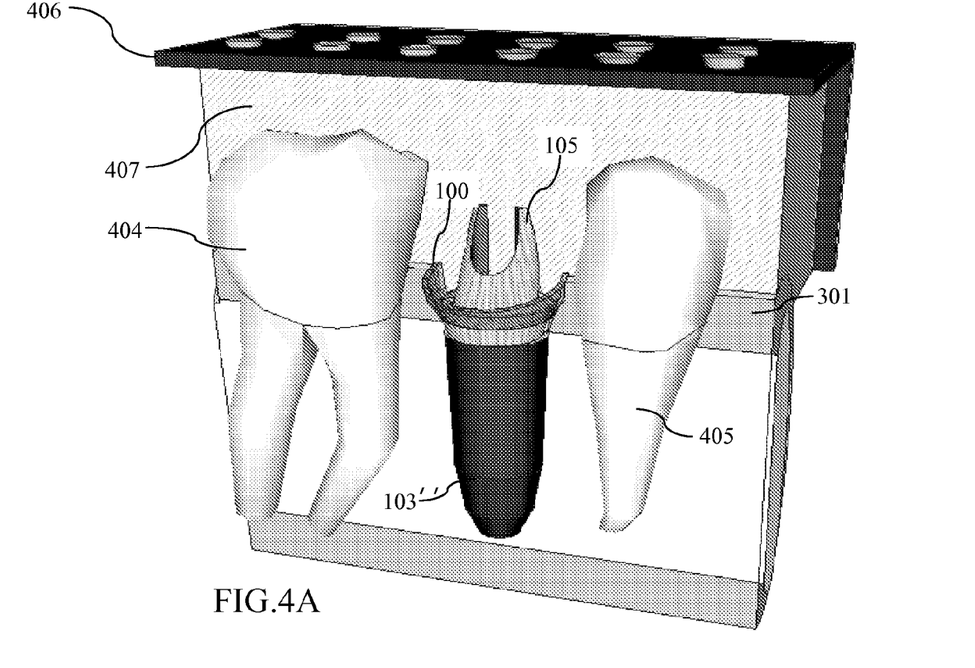
FIG. 4A Illustrates a section 2,2 of FIG. 4.

FIG. 4 and FIG. 4A illustrate the section 2,2 of the fragment of a patient's mouth to show the process of impression when the impression material 407 is in its fluid stage. The osteointegrated implant 103", situated between two natural teeth 404 and 405, equipped with the Impression Gingival Cuff 100 receives impression material 407 in the proximal end of the abutment 105. The impression tray 406 together with the impression material transmits hydraulic force to the adjacent teeth 404 and 405, soft tissue 301, abutment's proximal end 105, and to the Impression Gingival Cuff 100.

Figure 5:
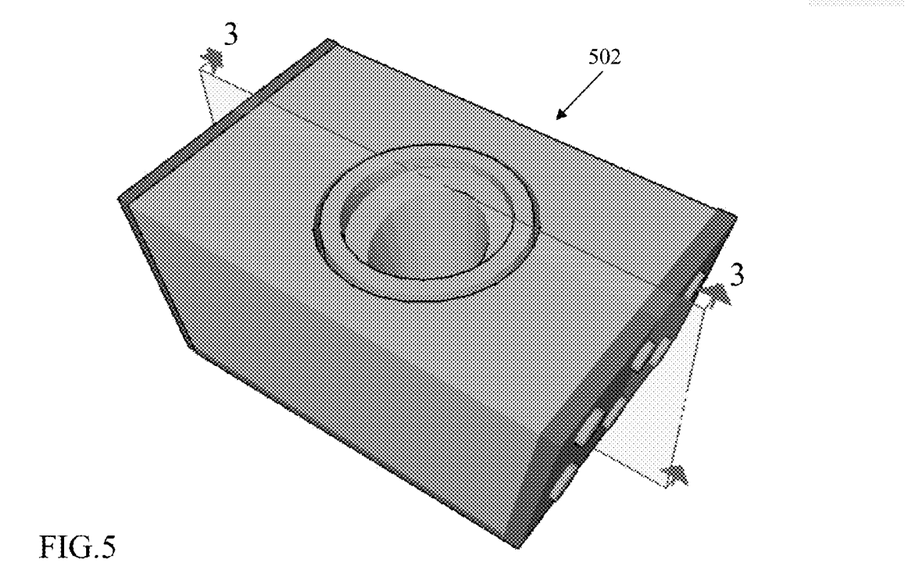
FIG. 5 illustrates a fragment of final implant impression taken with an aid of a Gingival
Figure 5A:
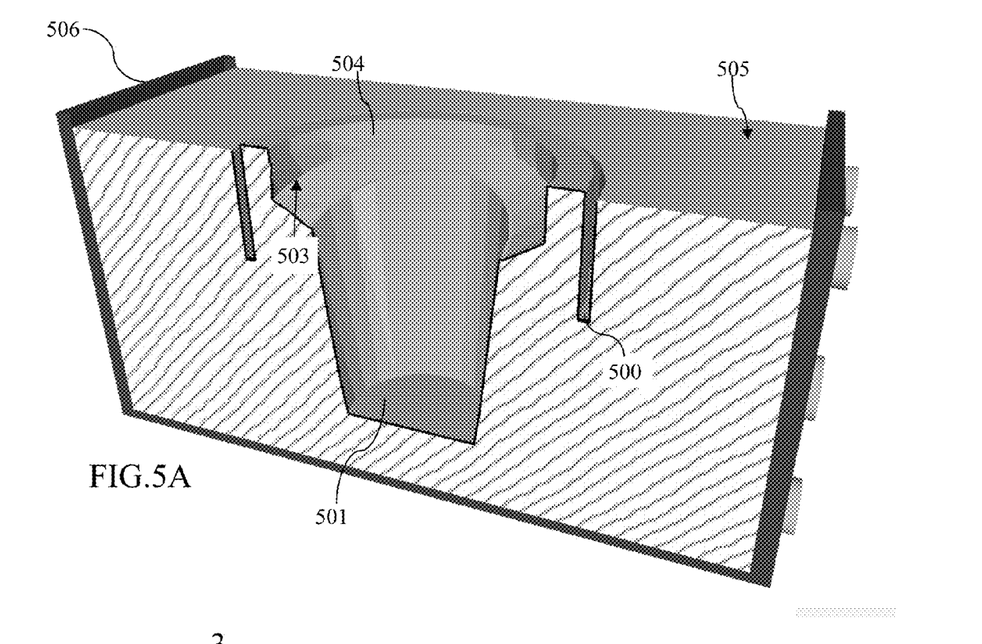
FIG. 5A illustrates a section 3,3 of FIG. 5.

FIG. 5 and FIG. 5A illustrate a section 3,3 of a negative mould 502 comprising an impression tray 506, Impression Gingival Cuff's registration 500, an abutment's body registration 501, a finish line registration 503, a small part of abutment's apical end registration 504, and a mucosal surface impression 505.

Figure 6:
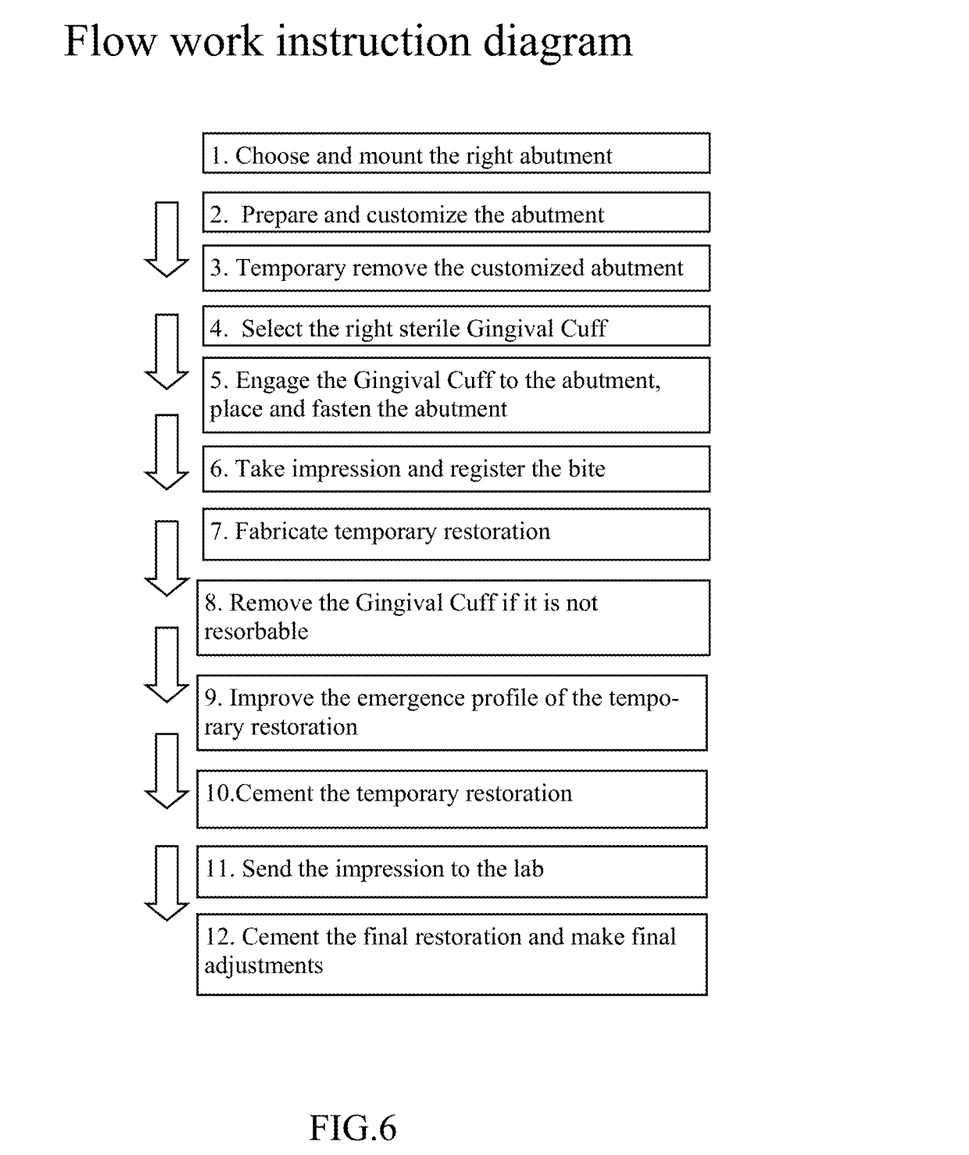
FIG. 6 Flow work instruction diagram.

FIG. 6 is a flow of instructions which are implemented with the method of taking impression of implant restoration using Impression Gingival Cuff.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

The invention can comprise, consist essentially of, or consist of the stated materials. The method can comprise, consist essentially of, or consist of the stated steps with the stated materials.

The foregoing has constituted a description of specific embodiments showing how the invention may be applied and put into use. These embodiments are only exemplary. The invention in its broadest and more specific aspects is further described and defined in the claims which follow.

These claims, and the language used therein are to be understood in terms of the variants of the invention which have been described. They are not to be restricted to such variants, but are to be read as covering the full scope of the invention as is implicit within the invention and the disclosure that has been provided herein.

What is claimed is:

1. A dental restoring system comprising:
   a dental implant osteointegrated in a jaw bone;
   an abutment having a prominent contour and a surface extending from the prominent contour in an apical direction, the abutment being engageably connectable to the dental implant;
   an impression gingival cuff for taking an impression during a restoration procedure, the impression gingival cuff comprising two open ends including an apical end with an apical opening oriented towards the apical direction and a proximal end with a proximal opening oriented towards an occlusal direction, an inner surface oriented towards the abutment and an outer surface oriented towards surrounding gingival tissue, the inner surface of the cuff shaped and sized to receive the surface of the abutment through the proximal opening of the cuff and to retain the abutment in the occlusal direction when the abutment is engaged to the implant; and
   an impression tray installed on a proximal end of the abutment for receiving impression material that transmits hydraulic force to the cuff to achieve an apical translation of the cuff and to allow the impression material to advance beyond the prominent contour in the apical direction while the outer surface of the impression gingival cuff pushes the surrounding gingival tissue away from the abutment.

2. The system of claim 1, wherein the surface of the abutment has a conical form.

3. The system of claim 1, wherein the surface of the abutment has a convex form.

4. The system of claim 1, wherein the impression gingival cuff is made of biocompatible materials comprising bioresorbable polymers, plastic polymers, or metal alloys.

5. The system of claim 1, wherein the inner and outer surfaces of the cuff are smooth to prevent adhesion to the impression material.

* * * * *